United States Patent [19]

Miller

[11] 4,050,470

[45] Sept. 27, 1977

[54] DENTAL FLOSS HOLDER AND APPLICATOR ASSEMBLY

[76] Inventor: Ercell Lynn Miller, 500 Westwood Ave., Columbia, Mo. 65201

[21] Appl. No.: 659,662

[22] Filed: Feb. 20, 1976

[51] Int. Cl.² ............................................ A61C 15/00
[52] U.S. Cl. ........................................ 132/89; 132/91
[58] Field of Search ............................. 132/89, 90, 91

[56] References Cited

U.S. PATENT DOCUMENTS

| 3,696,821 | 10/1972 | Adams | 132/91 |
| 3,901,251 | 8/1975 | Johnston | 132/91 |

Primary Examiner—G.E. McNeill
Attorney, Agent, or Firm—Schmidt, Johnson, Hovey & Williams

[57] ABSTRACT

A dental floss holder includes a pair of separate elongate grip members each provided with an inwardly tapered slot extending along one elongate edge thereof for positively engaging and retaining a length of dental floss such that the grip members can be easily secured in spaced relationship therealong to present convenient manual handles for facilitating the application of dental floss in an approved manner.

3 Claims, 4 Drawing Figures

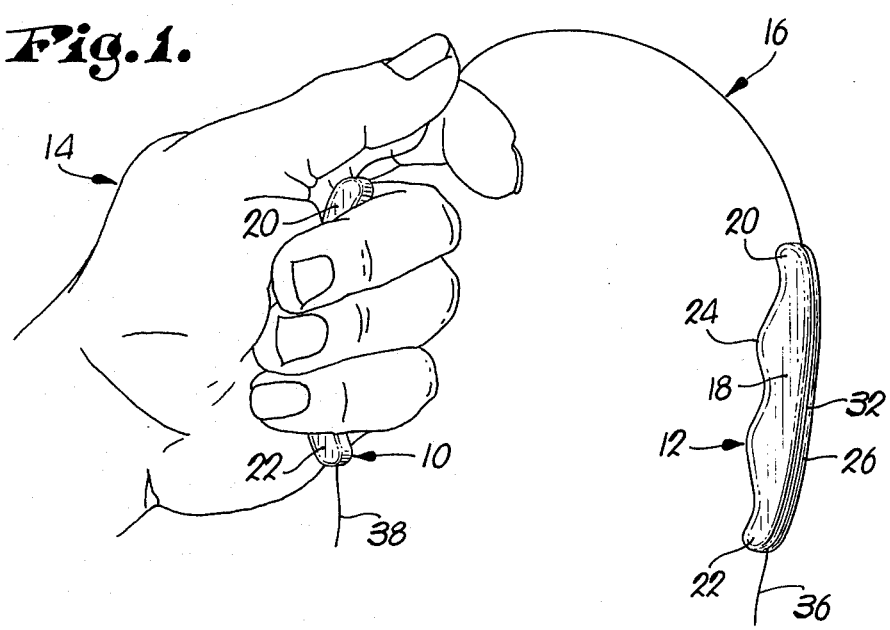
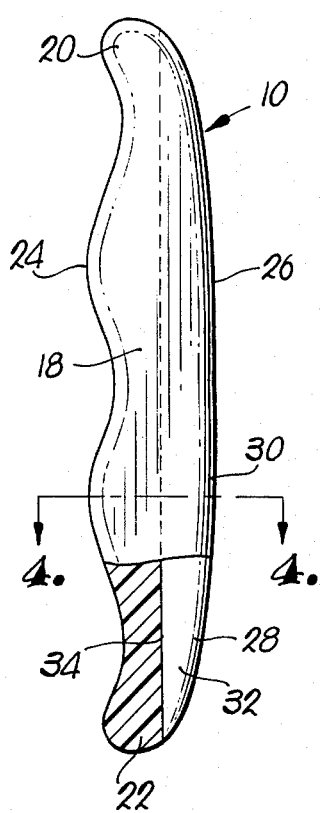
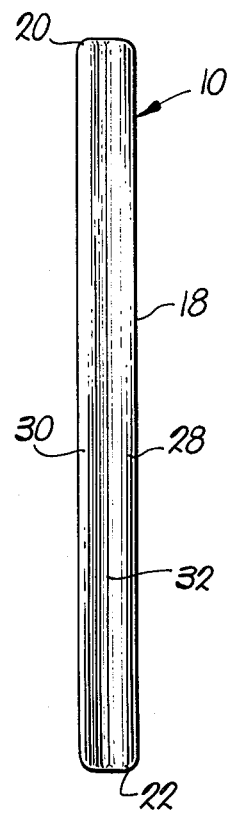
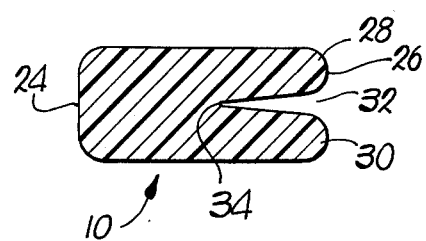

DENTAL FLOSS HOLDER AND APPLICATOR ASSEMBLY

This is a continuation-in-part of my co-pending application Ser. No. 587,073 filed June 16, 1975.

The invention disclosed herein concerns the mechanical holders of the type specifically adapted to assist in manual application of dental floss to human teeth using an accepted technique. Generally related devices are described, for example, in the U.S. patents to Moll U.S. Pat. No 2,648,341, Whitman U.S. Pat. No. 3,393,687 and Adams U.S. Pat. No. 3,696,821.

It is the most important object of this invention to provide a dental floss holder and applicator assembly comprising a pair of separate, elongate members adapted to be individually grasped by a hand of the user thereof, with the members being held in spaced-apart relationship and having a length of dental floss retained therebetween, whereby the assembly may be utilized in the generally accepted and recommended manner to remove bacterial plaque from the tooth surfaces of the user of the assembly.

It is yet a further important object of this invention to provide an assembly for use with a continuous length of dental floss whereby stretches of the floss may each be individually retained by a corresponding elongate member, each of the pair of members having an inwardly tapered slot formed in one elongate edge thereof to thereby retain the length of floss with respect to the members, thus permitting the members to be individually grasped by a hand of the user and the floss applied without the necessity of wrapping each end of the length of floss around the fingers of the user.

It is another important object of the present invention to provide a dental floss holder and applicator assembly as above wherein the tapered slots are the only required floss holding means such that the assembly may be used to apply the floss in the generally accepted manner and yet present the additional feature of permitting a quick and easy change of the length of floss when the same becomes frayed.

Other objects of this invention include the particular configuration of the separate elongate members and other details of construction and operation which will become apparent from the following specification and accompanying drawings, wherein:

FIG. 1 is a perspective view of the dental floss holder and applicator assembly, illustrating the manner in which one of the members is grasped by a hand of the user during use thereof;

FIG. 2 is an elevational view of one of the members;

FIG. 3 is an edge elevational view of one of the members with portions broken away to show construction details of the elongate slot; and FIG. 4 is an enlarged sectional view taken along line 4—4 of FIG. 2.

The dental floss holder and applicator assembly forming the subject matter hereof and completely shown in FIG. 1 of the drawing, includes a pair of separate, identical elongate members 10 and 12, which members are adapted to be positioned in spaced-apart relationship during use of the applicator, with each one of the members 10 and 12 being individually grasped by a corresponding hand of the user of the assembly. In FIG. 1, for instance, the member 10 is shown being grasped by the left hand 14 of the user, it being understood that member 12 would be likewise grasped in a corresponding fashion by the right hand of the user during application of the floss to the teeth. In use, a continuous length of dental floss 16 extends between the spaced-apart members 10 and 12 and is used to remove bacterial dental plaque from the tooth surface of the user of the assembly in a manner which will be hereinafter more particularly described.

Since the members 10 and 12 are identical in construction only one will be hereinafter described in detail, reference being made to FIGS. 2-5 wherein one of the elongate members, such as 10, is illustrated in detail. Thus, for instance, member 10, which is preferably molded from a suitable plastic material, has a central portion 18 and a pair of spaced-apart end portions 20 and 22. Central portion 18 as bounded by a pair of opposed edges 24 and 26 which extend between end portions 20 and 22. As shown in FIG. 2, edge 24 is undulated in a manner to present an ideal grip configuration for the fingers of the user; to additionally facilitate gripping, edge 26 is outwardly arcuate presenting a surface which readily fits against the palm of the user. Thus, for example, as shown in FIG. 1 the member 10 is preferably held in hand 14 with three fingers curled to grip edge 24 while the edge 26 is held against the palm of hand 14.

Member 10 is provided with retaining means in the form of a pair of spaced tabs 28, 30 which cooperate to define an elongate slot 32 extending along edge 26 for the entire length of member 10. As shown in FIG. 4, slot 32 gradually tapers inwardly to a closed end or bight 34 which forms a seat for securing a portion of the length of floss 16 adjacent one end thereof. At this point it is important to understand that bight 34 extends the entire length of member 10 thus providing a long seating area capable of positively retaining the floss 16. Accordingly, it is not necessary to provide any additional floss holding structure for the member 10. For reasons to be described hereinbelow, it is also important to note that member 10 has a transverse axis of symmetry such that the member 10 can function equally as well as in an inverted position.

To place the assembly in condition for use, member 12 is positioned adjacent one end 36 of the length of floss 16 and secured thereto by guiding a stretch of the floss 16 into slot 32 to seat against bight 34. In this regard, and in order to obtain a secure seating of the stretch of floss 16 within slot 32, it is contemplated that the transverse dimension of bight 34 will be smaller than the diameter of the floss 16. Member 10 is similarly secured to the length of floss 16 adjacent the other end 38 thereof. While ends 36 and 38 are shown as being the terminal portions of the length of floss 16, it is to be understood that either end 36 or 38 could be connected to a continuous supply of floss such as a spool or the like.

Once they have been placed in their proper relationship along the length of floss 16, the individual members 10 and 12 are then each grasped by a corresponding hand of the user of the assembly, it being noted that the length of each member 10 and 12 is sufficiently great to normally span three fingers of the hand such as 14 of the user whereby to permit the end portions 20 and 22 to extend oppositely beyond said three fingers. As described hereinabove, edges 24 and 26 cooperate to further aid in grasping the members 10 and 12 such that the user is provided with a comfortable yet positive grip on the members.

While holding the members 10 and 12 as above described, the user places a portion of the length of floss between the thumb and index finger of each hand in manner as shown for example, by the grasp of hand 14 in FIG. 1. This position allows proper application and manipulation of the length of floss 16 which spans the distance between members 10 and 12 when the same are in their spaced-apart applicator condition; the user may easily push upwardly with the thumbs against his upper teeth and downwardly with the index fingers against the lower teeth.

As the lengths of floss, such as 16, become frayed, they may be readily and quickly changed by substituting a new length of floss and subsequently securing the members 10 and 12 thereto in a manner described hereinabove. Alternatively, if the length of floss 16 remains connected to a spool or supply of floss at end 38, for example, a new length of floss may be obtained by extracting a desired length from the supply and permitting members 10 and 12 to slide along the floss until end 38 is beyond member 12 such that a new length of floss extends between member 12 and member 10. In this connection, the stretches of floss 16 seated in respective bights 34 of members 10 and 12 must first be pulled outwardly away from bights before the members 10 and 12 can be moved relative to the floss 16. Further in this regard, the members could also be conveniently emplaced in proper positions along a new length of floss by simply removing one of the members from the length of floss 16 and repositioning it or the new length of floss a desired distance from the other member. For example, if end 38 is connected to the floss supply, member 12 is merely repositioned to engage the new length of floss at a point spaced from end 22 of member 10; the latter remains emplaced adjacent end 38 but is grasped in an inverted position when applying the new length of floss to the teeth. Thus a new length of floss can be quickly positioned between members 10 and 12 in a desired arrangement by moving only one of the members. This "leapfrog" procedure may be easily and repeatedly performed without the necessity of cutting the floss since the members 10 and 12 do not require a free end of floss for proper initial securing thereto.

It should be noted that at no time is any portion of either member 10 or member 12 intended to enter the mouth of the user. Rather, the construction and manner of use of the assembly as hereinabove described, is such as to allow the index fingers and thumbs of each hand of the user to directly apply and manipulate the dental floss 16, while at the same time providing a comfortable and convenient grasp on the floss 16 without wrapping the floss around any part of the fingers or hand of the user.

Accordingly, the present invention provides a dental floss holder and applicator assembly which permits the user to simply and conveniently remove bacterial dental plaque from the tooth surfaces of the user in a manner highly recommended by the dental profession. The unique floss retaining means provided in the individual grip members of the present invention not only assures that substantially the entire length of floss is efficiently utilized, but also permits extremely fast and effective positioning of the grip members in their proper locations along a length of floss. In this connection, the members 10 and 12 of the present invention are not burdened with complicated floss-engaging structure requiring tying, threading, or other operator manipulations to secure the floss thereto, but rather the members 10 and 12 are simply provided with a single elongate tapered slot as the sole, yet extremely effective, floss gripping means. This construction makes available the "leapfrog" technique for repositioning the floss as described hereinabove.

Having thus described the invention, what is new and desired to be secured by Letters Patent is:

1. A dental floss holder and applicator assembly comprising:
    a pair of separate, elongate members, each of said members being adapted to be individually grasped within a hand of a user whereby to position said members in spaced apart relationship during application of the floss to the user's teeth;
    a length of floss extending between said members when the assembly is in use;
    a pair of spaced apart end portions on each member, the distance between said end portions being sufficiently great to normally permit grasping of each member by three fingers of the hand of the user with the end portions extending oppositely beyond said three fingers;
    retaining means on each member extending the length thereof between said end portions, said retaining means comprising a slot formed in said member along one elongate edge thereof.

2. A dental floss holder and applicator assembly as claimed in claim 1, wherein said slot is inwardly tapered.

3. A dental floss holder and applicator assembly as claimed in claim 2, wherein said one edge is arcuate.

* * * * *